United States Patent [19]

Mauersberger

[11] Patent Number: 4,936,673
[45] Date of Patent: Jun. 26, 1990

[54] DIFFUSION PLATELET IN COMBINATION WITH A SLIT LAMP

[75] Inventor: Udo Mauersberger, Aalen, Fed. Rep. of Germany

[73] Assignee: Carl-Zeiss-Stiftung, Heidenheim/Brenz, Fed. Rep. of Germany

[21] Appl. No.: 371,458

[22] Filed: Jun. 26, 1989

[30] Foreign Application Priority Data

Jul. 9, 1988 [DE] Fed. Rep. of Germany ... 8808871[U]

[51] Int. Cl.$^5$ .......................... A61B 3/10; A61B 3/14
[52] U.S. Cl. ..................................... 351/214; 351/206

[58] Field of Search ....................... 351/205, 206, 214; 354/62

[56] References Cited

U.S. PATENT DOCUMENTS 3,944,343 3/1976 Mueller ............................. 351/214

Primary Examiner—Rodney B. Bovernick
Attorney, Agent, or Firm—Stonebraker, Shepard & Stephens

[57] ABSTRACT

This invention relates to slit lamps of the type incorporated in instruments used to illuminate eyes for ophthalmic examination and/or photography; and, more particularly, it relates to controlling the illumination produced by such slit lamps.

6 Claims, 1 Drawing Sheet

# DIFFUSION PLATELET IN COMBINATION WITH A SLIT LAMP

BACKGROUND

This invention relates to slit lamps of the type incorporated in instruments used to illuminate eyes for ophthalmic examination and/or photography; and, more particularly, it relates to controlling the illumination produced by such slit lamps.

In such instruments, the eye being examined is illuminated from the side by an angularly adjustable slit lamp. The illumination emerges from a narrow end surface of the lamp's illuminating prism and is normally diffused to increase the area of the illumination impinging on the target. In prior art devices, such diffusion has been accomplished by means of a ground glass platelet placed over the surface of the prism edge from which the illumination emerges. The roughened surfaces of such prior art platelets are produced by grinding with an abrasive, or by etching, or by grinding followed by etching.

As is well-known in the art, the grain size of the abrasive, or the etching technique, can be varied to determine the resulting granularity (roughness) which is distributed irregularly over the surface of the ground glass. The degree of such roughness, in turn, determines the angles of diffusion and the character of the resulting illumination.

Although such prior art ground glass platelets serve to diffuse the illumination of the slit lamp over larger areas, the random irregularity of the platelet surface results in significant light losses, because the area of illumination does not conform well to the oval area of the eye's palpebral fissure (i.e., the area between the margins of the eyelids when the eye is open). That is, such slit lamp illumination suffers from a vignetting effect and does not adequately illuminate the ends of this oval area. This is particularly noticeable when using prior art slit lamp illumination for purposes of reproducing the palpebral fissure photographically because proper exposure of the central portion of the oval is often accompanied by insufficient exposure of its end portions.

SUMMARY OF THE INVENTION

The invention herein modifies the design of the ground glass platelet to produce a preferentially directed diffusion characteristic for the illumination of the slit lamp, namely, the illumination is diffused in a radiation pattern which more nearly conforms to the oval shape of the eye being examined.

This desired result is accomplished in a relatively simple manner: the surface of the glass platelet which faces toward the light emergence surface of the slit lamp's illuminating prism is ground in the known manner to have an irregular ground glass granularity. However, the backside of the platelet, which faces away from the illuminating prism, is ground only in its longitudinal direction with an abrasive of defined grain size so that this surface is characterized by irregularly-spaced, longitudinal grooves.

In the preferred embodiment of the invention, the novel ground glass platelet is pivotally mounted to the body of the slit lamp instrument so that it can be pivoted into or out of its operative position in front of the illuminating prism.

DRAWINGS

DETAILED DESCRIPTION

Figure 1:
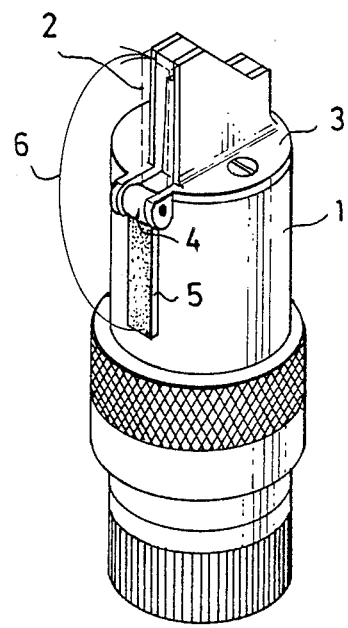
FIG. 1 is a perspective view of the body tube of a slit lamp instrument showing the light emergence prism and the diffusion platelet.

Referring to FIG. 1, the body tube 1 of a slit lamp instrument carries an illuminating prism with a light emergence surface 2. Attached to body tube 1 is a holder 3 which receives the pivot bearing 4 of the invention's diffusion platelet 5. As indicated by arrow 6, the platelet 5 is pivotable between an inoperative position, as shown in FIG. 1, to an operative position in front of the light emergence surface 2 of the illuminating prism.

Figure 2A:
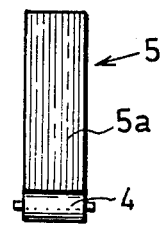
FIG. 2a is a plan view of the backside of the diffusion platelet.
Figure 2B:
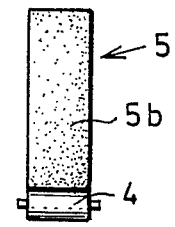
FIG. 2b is a plan view of the front of the diffusion platelet.

As can be seen from FIGS. 2a and 2b, the front surface 5a of platelet 5 has longitudinal grooves which have been ground using an abrasive of defined grain size. In the preferred form of the invention, these grooves are irregularly spaced, and it has been determined empirically that the best results are obtained by grinding surface 5a using an abrasive paper with a grain size of 80.

The back surface 5b of the platelet 5 is prepared in the known manner to possess the irregular granularity of conventional ground glass.

When platelet 5 is pivoted to its operative position in front of the slit lamp's prism, it produces an oval radiation characteristic in the object plane which provides illumination of the entire palpebral fissure without undesirable vignetting of the end portions of the oval.

I claim:

1. In a slit lamp instrument having an illuminating prism with a light emergence surface, said instrument also having light-diffusing means including a ground glass platelet positionable in front of said light emergence surface, said platelet, when so positioned, having a first surface facing toward said light emergence surface and a second surface facing away from said light emergence surface, the improvement wherein the ground glass surface of the first surface of said platelet has an irregular granularity and the surface of the second surface of said glass platelet has longitudinal grooves.

2. The slit lamp instrument of claim 1 wherein said longitudinal grooves are irregularly spaced.

3. The slit lamp instrument of claim 2 wherein said longitudinal grooves in the second surface of said glass platelet are produced by grinding with an abrasive.

4. The slit lamp instrument of claim 3 wherein said abrasive is paper having a grain size of 80.

5. The slit lamp instrument of claim 1 wherein said ground glass platelet is movable from said position in front of said light emergence surface to an inoperable position in which said first surface does not face toward said light emergence surface.

6. The slit lamp instrument of claim 5 wherein said ground glass platelet is mounted to said instrument so that it pivots from said inoperative position to an operative position in front of said light emergence surface of the illuminating prism.

* * * * *